United States Patent [19]

Saphores et al.

[11] Patent Number: 5,011,965
[45] Date of Patent: Apr. 30, 1991

[54] PROCESS FOR PRODUCTION OF METHYLENE BISXANTHATES

[75] Inventors: Eugenio A. Saphores; Arturo G. Gleisner, both of Vina del Mar; Juan C. Vega; Wladimir A. Mardones, both of Santiago, all of Chile

[73] Assignee: Establecimientos Industriales Quimicos Oxiquim S.A., Vina del Mar, Chile

[21] Appl. No.: 344,912

[22] Filed: Apr. 28, 1989

[51] Int. Cl.$^5$ ............................................. C07C 327/36
[52] U.S. Cl. ..................................... 558/245; 558/246
[58] Field of Search ................................ 558/245, 246

[56] References Cited
U.S. PATENT DOCUMENTS 3,011,887 12/1961 Cupery et al. ...................... 558/245
3,667,931 6/1972 Viste et al. ............................ 558/245

OTHER PUBLICATIONS

Dehmlow, et al., Phase Transfer catalysis, Verlag Chemie, Deerfield Beach, FL., 1980, p. 74.

Primary Examiner—Mary C. Lee
Assistant Examiner—Robert C. Whittenbaugh
Attorney, Agent, or Firm—Mallinckrodt & Mallinckrodt

[57] ABSTRACT

A methylene bisxanthate chemical compound is produced by reaction of an aqueous solution of an alkaline xanthate with methylene chloride in the presence of a polyethylene glycol (PEG) with alcoholic terminal groups as a phase transfer catalyst. The PEG is water soluble and may be recovered and recycled in the process. The reaction product may be purified, but can be used in the crude state as a collector reagent in the froth flotation of sulfide minerals, or of sulfidized oxide minerals, from their ores.

11 Claims, No Drawings

PROCESS FOR PRODUCTION OF METHYLENE BISXANTHATES

BACKGROUND OF THE INVENTION

1. Field:

The invention is concerned with the industrial production of methylene bisxanthates and with uses for such chemical compounds.

2. State of the Art:

It is known that methylene bis ethylxanthate can be produced by reacting methylene bromide with potassium ethylxanthate in acetone, see U.S. Pat. No. 3,011,887, and that this chemical compound is useful as a defoliant for cotton plants. It is also known that this chemical compound, as well as methylene bis propylxanthate, is useful as an herbicide in rice cultivation, see U.S. Pat. No. 3,667,931.

SUMMARY OF THE INVENTION

In accordance with the present invention, it has been found that methylene bisxanthates represented by the general formula

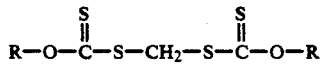

wherein R is an alkyl group, such compounds sometimes being called methane bis (alkoxythiocarbonylthio), can be economically produced on an industrial basis (and are especially useful as collectors for sulfide minerals in the froth flotation of ores as set forth in our concurrently filed U.S. application Ser. No. 07/344,913) by reacting an aqueous solution of an alkaline xanthate with methylene chloride in the presence of polyethylene glycol (generally referred to as PEG) as a phase transfer catalyst.

Such a reaction is represented by the general formula:

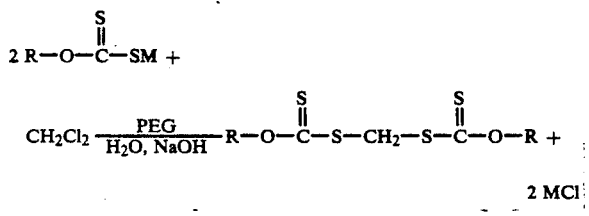

wherein R is an alkyl group of one to six carbon atoms, M is an alkaline metal, preferably sodium or potassium, and PEG is a polyethylene glycol catalyst with terminal alcoholic groups conforming to the general formula:

preferably wherein n is a whole number approximately in the range of 14 to 30.

Since the PEG catalyst is highly water soluble, it can be easily separated from the organic phase of the reacted materials for recycling in the process by a simple water extraction.

Thus, the process is based on the reaction of an alkaline xanthate with methylene chloride at reflux temperature accompanied by vigorous agitation in the presence of the polyethylene glycol having a molecular weight in the range of approximately 600-6000. This forms a liquid system made up of an aqueous phase containing alkaline xanthate and a solution of from 10 to 50% sodium or potassium hydroxide depending upon which alkaline metal is present, in quantity of at least 0.1 moles per mol of xanthate, and an organic phase containing methylene chloride and the polyethylene glycol.

After filtration of solids, separation of phases, and distillation of the remaining methylene chloride, a mixture of methylene bisxanthate and the PEG catalyst is obtained. The methylene bisxanthate is obtained as an end product by water extraction of the polymer.

DETAILED DESCRIPTION OF PREFERRED EMBODIMENT

The best mode presently contemplated for carrying out the invention in commercial practice is set forth herein as a preferred embodiment of the invention and as indicative of the various ways those skilled in the art can apply the invention in particular instances within the scope of the claims thereto.

Thus, in producing a methylene bisxanthate, it is preferred to either prepare, as a starting material, an alkaline xanthate by conventional procedures well known to those skilled in the art, or to use an already prepared technical grade of an alkaline xanthate, usually a sodium xanthate, such as an aqueous solution of sodium isopropylxanthate. Preparation of an alkaline xanthate starting material can be carried out by reacting sodium hydroxide, carbon disulfide, and isopropyl alcohol under appropriate conditions known to the art.

To the alkaline xanthate is added methylene chloride, a catalytic amount of the PEG 600-6000, and water, and this mixture, along with an aqueous solution of from about ten to about fifty percent sodium hydroxide, is heated at reflux temperature of from about 41° to about 43° C. for about two to ten hours accompanied by vigorous stirring. The methylene chloride acts as both a solvent and reactant for the ionic compounds in the mixture.

The amount of methylene chloride used is not critical so long as enough is present to carry out the desired reaction productive of a methylene bisxanthate. Any excess is removed by distillation of the organic phase of the reaction mixture, which is separated from the water content, as by decantation, after filtration of such reaction mixture to remove insoluble solids.

The molar ratio between the xanthate and the PEG is 1.0 to 0.001–0.1 depending upon the strength of the PTC used, and the quantity of the hydroxide is at least 0.2 mols. per mol. of xanthate.

Following distillation of the reaction mixture, leaving a residual of methylene bisisopropylxanthate and the PEG, water is added as a washing medium, the resulting mix stirred, and the water and the PEG removed, as by decantation. This yields a crude methylene bisisopropylxanthate that may be used as is as a collector reagent in a process of froth flotation or for whatever other use may be found for it. The recovered PEG can and preferably is recycled in the process.

It should be noted that the use of methylene chloride in the present process, instead of methylene bromide as used in the process of the afore-noted U.S. Pat. No. 3,011,887, is highly advantageous because the chloride is a solvent that is readily available at significantly lower cost than the bromide. Moreover, chloride ions do not contaminate as bromide ions do.

The use of a polyethylene glycol (PEG) as a phase transfer catalyst is highly desirable because of low cost, non-toxicity, and easy handling and recycling.

The following are typical examples of the process in accordance with preferred practice:

EXAMPLE NO. 1

Into a three-necked flask equipped with a mechanical stirrer and a water jacket as a condenser, was charged 1 mol. of sodium isopropylxanthate (198 grs, 80% purity), 100 mls of water, 500 mls of methylene chloride, 80 grs of 50% sodium hydroxide aqueous solution, and 30 grs of 1,000 average molecular weight PEG glycol (0.03 mols.). This mixture was heated at reflux temperature (41°–43° C.) for 6 hours with vigorous stirring. The resulting reaction mixture was then filtered to remove insoluble solids, and the organic and water layers were separated. The organic phase was distilled to remove unreacted methylene chloride, and a mixture of methylene bisisopropylxanthate and PEG 1000 remained. To this were added 40 mls of water. The resulting mixture was stirred and then left for subsequent decantation of the separated upper layer. The organic layer contained the crude methylene bisisopropylxanthate (1.28 grs, 90% yield) reaction product. Purification of this product through a silica gel column gave a colorless, viscous liquid which had elemental analysis and spectral characteristics in accordance with its known structure.

EXAMPLE NO. 2

In the same equipment and in a similar manner, 1 mol. of sodium ethylxanthate (160 grs, 90% purity) was treated with 70 mls of water, 350 mls of $CH_2Cl_2$, 80 grs of 50% aqueous NaOH solution, and 15 grs of PEG 1,500 (0.01 molar). After a 5 hour heating period, with vigorous stirring and separation as in Example No. 1, a quantity (122 grs 95% yield) of crude methylene bis ethylxanthate was obtained. Crystallization of this product from added ethanol, yielded a white solid which melted at 37°–39° C. (literature melting point is 37° C.).

EXAMPLE NO. 3

In manner similar to that of Example No. 1, a quantity (198 grs.) of sodium isobutylxanthate (1 mol., 87% purity) was reacted with 600 mls of $CH_2Cl_2$, 120 mls of water, 80 grs of 50% NaOH aqueous solution, and 60 grs of PEG 3,000 (0.02 mols.). After heating at reflux temperature and stirring for seven hours, the crude reaction mixture was subjected to the same steps of purification as in Example No. 1, with the exception that PEG 3000 was used. This was done twice with 50 mls each. The organic residue was 144 grs (93% yield) of methylene bisisobutylxanthate, which was purified as in Example No. 1 giving a colorless viscous liquid with elemental analysis and spectral properties in agreement with its structure.

For use as a collector reagent in the froth flotation of sulfide minerals or of sulfidized oxide minerals, it is unnecessary to go through the purification stages. The crude methylene bisxanthate reaction product is used without any need for purification.

Whereas this invention is here illustrated and described with specific reference to an embodiment thereof presently contemplated as the best mode of carrying out such invention in actual practice, it is to be understood that various changes may be made by those skilled in the art in adapting the invention to different embodiments, without departing from the broader inventive concepts disclosed herein and comprehended by the claims that follow.

We claim:

1. A process for producing a methylene bisxanthate, comprising reacting an aqueous solution of an alkaline xanthate with methylene chloride in the presence of PEG with terminal alcoholic groups as a phase transfer catalyst in accordance with the following formula:

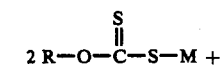

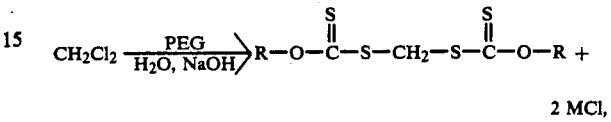

2 MCl, wherein R is an alkyl group containing from one to six carbon atoms and M is an alkaline metal; and separating the resulting methylene bisxanthate reaction product from other components of the reaction mixture.

2. A process according to claim 1, wherein the polyethylene glycol conforms to the general formula

wherein n is a whole number approximately with the range of 14 to 30.

3. A process according to claim 1, wherein M is sodium.

4. A process according to claim 1, wherein M is potassium.

5. A process according to claim 1, wherein the PEG is polyethylene glycol in the range of from 0.001 to 0.1 mols. per mol. of xanthate.

6. A process according to claim 1, wherein the $H_2O$ NaOH is in the range of from ten to fifty percent sodium hydroxide.

7. A process according to claim 1, wherein the alkaline xanthate is an aqueous suspension of sodium isopropylxanthate.

8. A process according to claim 1, wherein an effective amount of the methylene chloride, the alkaline xanthate, and the PEG are mixed together with an effective quantity of a fifty percent sodium hydroxide solution and heated at reflux temperature in about the range of 41° to 43°degrees C. for from about two to about ten hours while being vigorously stirred.

9. A process according to claim 8, wherein the bisxanthate reaction product is separated from the reaction mixture by first filtering the reaction mixture to remove insoluble solids therefrom; removing water from the reaction mixture to provide a substantially water-free organic phase; distilling said organic phase to remove any unreacted methylene chloride, leaving the methylene bisxanthate reaction product mixed with the PEG; washing that mixture with water to dissolve the PEG; and separating the wash water, containing the PEG, from the methylene bisxanthate reaction product.

10. A process according to claim 9, wherein the PEG is removed from the was water and recycled in the process.

11. A process according to claim 1, wherein the reaction mixture contains the PEG catalyst, which is separated from the remainder of said reaction mixture and is recycled in the process.

* * * * *